United States Patent
Agnesi et al.

(10) Patent No.: US 10,188,865 B2
(45) Date of Patent: Jan. 29, 2019

(54) SYSTEMS AND METHODS OF COMBINED TONIC DBS AND RANDOM DBS

(71) Applicant: PACESETTER, INC., Sylmar, CA (US)

(72) Inventors: Filippo Agnesi, Plano, TX (US); Lalit Venkatesan, Prosper, TX (US)

(73) Assignee: PACESETTER, INC., Sylmar, CA (US)

( * ) Notice: Subject to any disclaimer, the term of this patent is extended or adjusted under 35 U.S.C. 154(b) by 243 days.

(21) Appl. No.: 15/183,478

(22) Filed: Jun. 15, 2016

(65) Prior Publication Data

US 2017/0361105 A1 Dec. 21, 2017

(51) Int. Cl.
*A61N 1/00* (2006.01)
*A61N 1/36* (2006.01)
*A61N 1/05* (2006.01)

(52) U.S. Cl.
CPC ....... *A61N 1/36178* (2013.01); *A61N 1/0534* (2013.01); *A61N 1/36067* (2013.01); *A61N 1/36125* (2013.01); *A61N 1/36185* (2013.01)

(58) Field of Classification Search
CPC ............ A61N 1/36178; A61N 1/36185; A61N 1/0534; A61N 1/36067; A61N 1/36125
See application file for complete search history.

(56) References Cited

U.S. PATENT DOCUMENTS

| | | |
|---|---|---|
| 9,764,135 B2 | 9/2017 | De Ridder |
| 2011/0009923 A1* | 1/2011 | Lee .................... A61N 1/36071 607/46 |
| 2012/0059438 A1 | 3/2012 | De Ridder |

OTHER PUBLICATIONS

Zeitler et al.;Frontiers in Computational Neuroscience; Antikindling Induced by Two-Stage Coordinated Reset Stimulation with Weak Onset Intensity; May 2016 | vol. 10 | Article 44.

* cited by examiner

*Primary Examiner* — Mallika D Fairchild

(57) ABSTRACT

The present disclosure provides systems and methods for combining tonic deep brain stimulation (DBS) and random DBS. A system includes a stimulation lead including a plurality of contacts, and an implantable pulse generator (IPG) communicatively coupled to the stimulation lead and configured to cause tonic stimulation to be delivered using one contact of the plurality of contacts, and cause random stimulation to be delivered using a subset of the remaining contacts of the plurality of contacts.

7 Claims, 5 Drawing Sheets

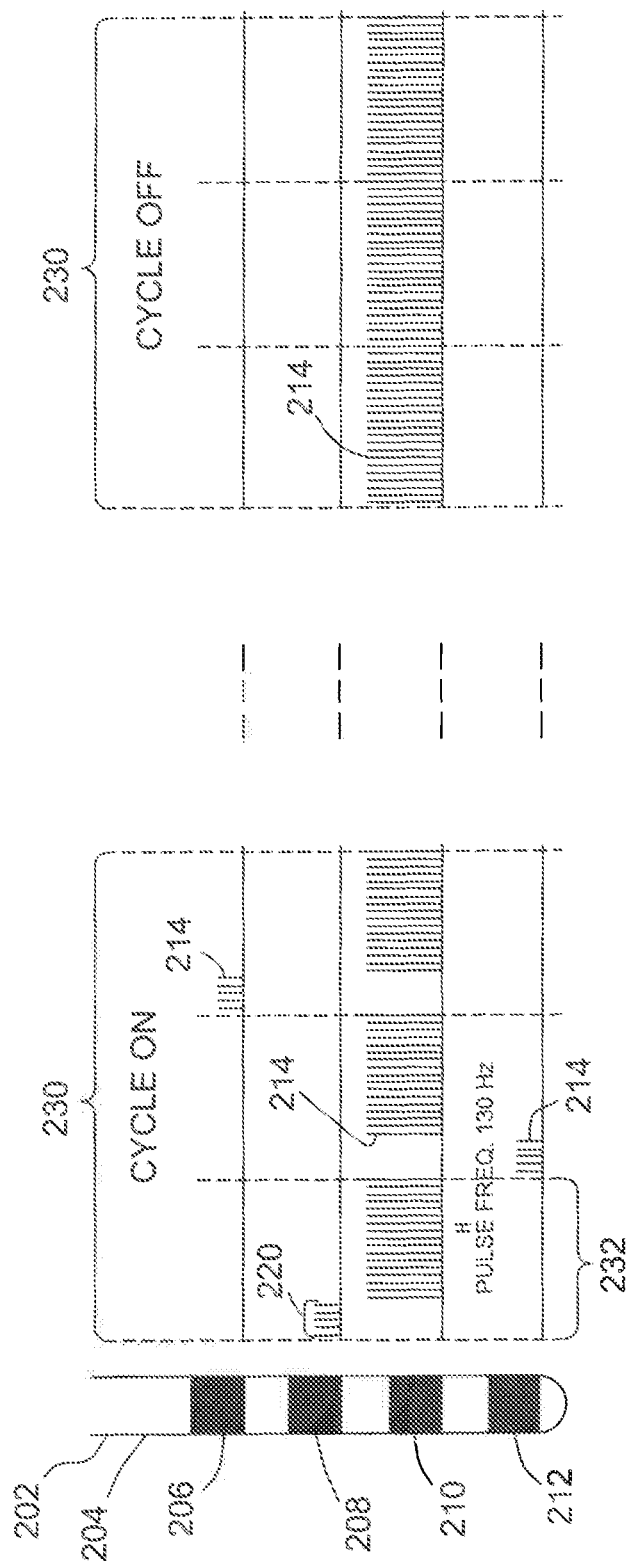

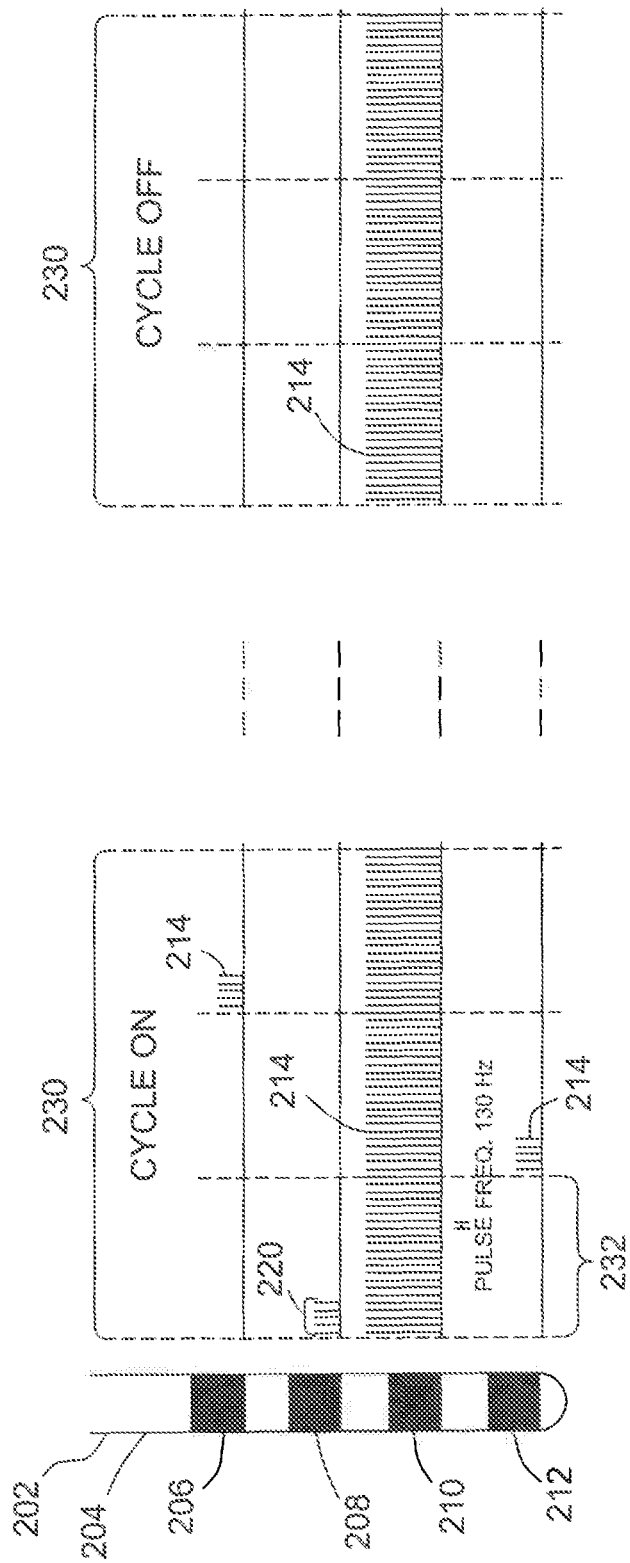

SYSTEMS AND METHODS OF COMBINED TONIC DBS AND RANDOM DBS

FIELD OF THE DISCLOSURE

The present disclosure relates generally to deep brain stimulation (DBS) systems, and more particularly to combining tonic and random stimulation.

BACKGROUND ART

Deep brain stimulation (DBS) is an established neuromodulation therapy for the treatment of movement disorders, and has been shown to improve cardinal motor symptoms of Parkinson's Disease (PD), such as bradykinesia, rigidity, and tremors. These improvements generally occur within a few minutes of initiation of stimulation, and disappear within a similar timeframe after stimulation is discontinued. DBS may include using tonic stimulation to deliver high-frequency isochronal electrical pulses (e.g., at a pulse frequency of 130-180 Hertz (Hz) with a pulse width of 20-200 microseconds) through a single contact electrode implanted in the Basal ganglia thalamo-cortical "motor circuit" of the brain.

In brain activity, abnormal synchronization of neuronal activity is an indicator of various movement disorders, such as PD. Studies have shown that PD is associated with increase oscillations in the beta band, which has been associated with bradykinesia and rigidity. Further, research has suggested that such abnormal synchronization may be disrupted by delivering short sequences of stimulation pulses through different electrodes activated at different times in random order. This may provide sustained amelioration of rigidity and bradykinesia, especially after multiple stimulation sessions. However such random stimulation may not be as effective as tonic stimulation, and may not ameliorate tremors, which may be severely disabling for a patient.

BRIEF SUMMARY OF THE DISCLOSURE

In one embodiment, the present disclosure is directed to a deep brain stimulation (DBS) system for delivering a combination of tonic stimulation and random stimulation. The DBS system includes a stimulation lead including a plurality of contacts, and an implantable pulse generator (IPG) communicatively coupled to the stimulation lead and configured to cause tonic stimulation to be delivered using one contact of the plurality of contacts, and cause random stimulation to be delivered using a subset of the remaining contacts of the plurality of contacts.

In another embodiment, the present disclosure is directed to an implantable pulse generator (IPG) for use with a deep brain stimulation (DBS) system for delivering a combination of tonic stimulation and random stimulation. The IPG includes a memory device, and a controller communicatively coupled to the memory device, the controller configured to cause stimulation to be delivered to a patient using a plurality of contacts of a stimulation lead coupled to the IPG by causing tonic stimulation to be delivered using one contact of the plurality of contacts, and causing random stimulation to be delivered using a subset of the remaining contacts of the plurality of contacts.

In another embodiment, the present disclosure is directed to a method of applying a combination of tonic stimulation and random stimulation using a stimulation lead including a plurality of contacts. The method includes delivering tonic stimulation using one contact of the plurality of contacts, and delivering random stimulation using a subset of the remaining contacts of the plurality of contacts.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 4 is a schematic diagram illustrating one embodiment of application of a combination of tonic DBS and random DBS using a stimulation lead.

FIG. 5 is a schematic diagram illustrating another embodiment of application of a combination of tonic DBS and random DBS using a stimulation lead.

Corresponding reference characters indicate corresponding parts throughout the several views of the drawings.

DETAILED DESCRIPTION OF THE DISCLOSURE

The present disclosure provides systems and methods for combining tonic and random stimulation in a deep brain stimulation (DBS) system. A stimulation lead includes a plurality of contacts. An implantable pulse generator (IPG) communicatively coupled to the stimulation lead causes tonic stimulation to be delivered using one contact of the plurality of contacts, and cause random stimulation to be delivered using a subset of the remaining contacts of the plurality of contacts. The applied stimulation yields the benefits of both random and tonic stimulation.

Neurostimulation systems are devices that generate electrical pulses and deliver the pulses to nerve tissue of a patient to treat a variety of disorders. One category of neurostimulation systems is deep brain stimulation (DBS). In DBS, electrical pulses are delivered to parts of a subject's brain, for example, for the treatment of movement and effective disorders such as PD and essential tremor.

Neurostimulation systems generally include a pulse generator and one or more leads. A stimulation lead includes a lead body of Insulative material that encloses wire conductors. The distal end of the stimulation lead includes multiple electrodes, or contacts, that are electrically coupled to the wire conductors. The proximal end of the lead body includes multiple terminals (also electrically coupled to the wire conductors) that are adapted to receive electrical pulses. In DBS systems, the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted within a subcutaneous pocket created during the implantation procedure.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Figure 1:
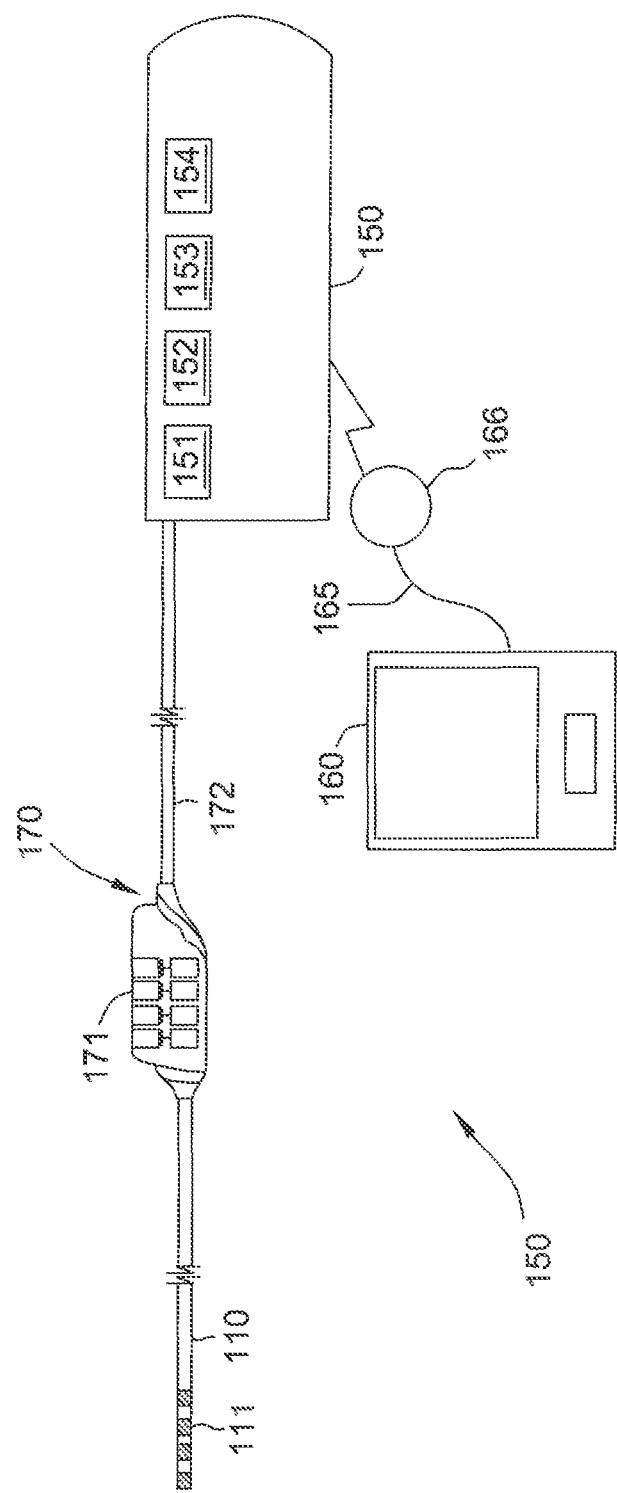
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. IPG 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. In the methods and systems described herein, parameters may include, for example, a number of pulses in a burst (e.g., 3, 4, or 5 pulses per burst), an intra-burst frequency (e.g., 130 Hz), an inter-burst frequency (e.g., 3-20 Hz), and a delay between a first and second burst (e.g., less than 1 millisecond (ms)).

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from St. Jude Medical, Inc. (Plano, Tex.).

The systems and methods described herein use both tonic DBS and random DBS to facilitate treating symptoms of PD and other movement and effective disorders. Further, the embodiments described herein exploit the cumulative effects of multiple random DBS stimulation sessions, ultimately reducing overall stimulation needs of patients. Specifically, tonic DBS is delivered using one or more contacts (i.e., electrodes) and parameters identified during therapy optimization, and a subset of the remaining available contacts are used to deliver a randomized stimulation pattern. A subset may include all of the remaining available contacts or less than all of the remaining available contacts. The tonic and randomized stimulation patterns are interleaved to prevent the therapeutic effect of tonic DBS from being compromised by discontinuities associated with random DBS. Accordingly, tonic DBS and random DBS are combined to achieve the advantages of both.

Figure 2:
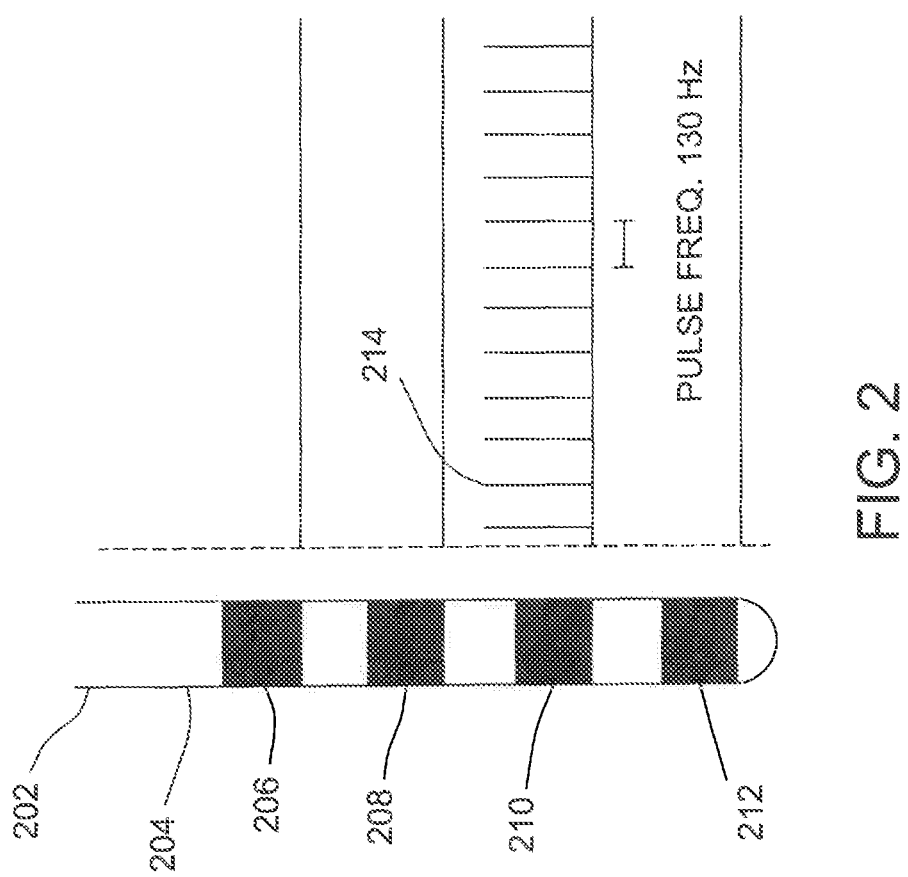
FIG. 2 is a schematic diagram illustrating one embodiment of application of tonic DBS using a stimulation lead.

FIG. 2 is a schematic diagram illustrating application of tonic DBS using a stimulation lead 202. Stimulation lead 202 may be used, for example, with neurostimulation system 100 (shown in FIG. 1) to apply the tonic DBS. In this embodiment, stimulation lead 202 includes a distal segment 204 that includes a first contact 206, a second contact 208, a third contact 210, and a fourth contact 212. Alternatively, distal segment 204 may include any suitable number of contacts, or electrodes. Contacts 206, 208, 210, and 212 may be, for example, ring electrodes or segmented electrodes. Stimulation lead 202 may be positioned, for example, within a subthalamic nucleus (STN) of the patient.

In this embodiment, to apply tonic DBS, third contact 210 delivers stimulation pulses 214 at a constant frequency (e.g., 130 Hertz (Hz)). Although in this embodiment, third contact 210 delivers stimulation, alternatively, any of contacts 206, 208, 210, and 212 may be used to deliver stimulation. The contact used to deliver tonic stimulation may be selected, for example, during a therapy optimization session.

Figure 3:
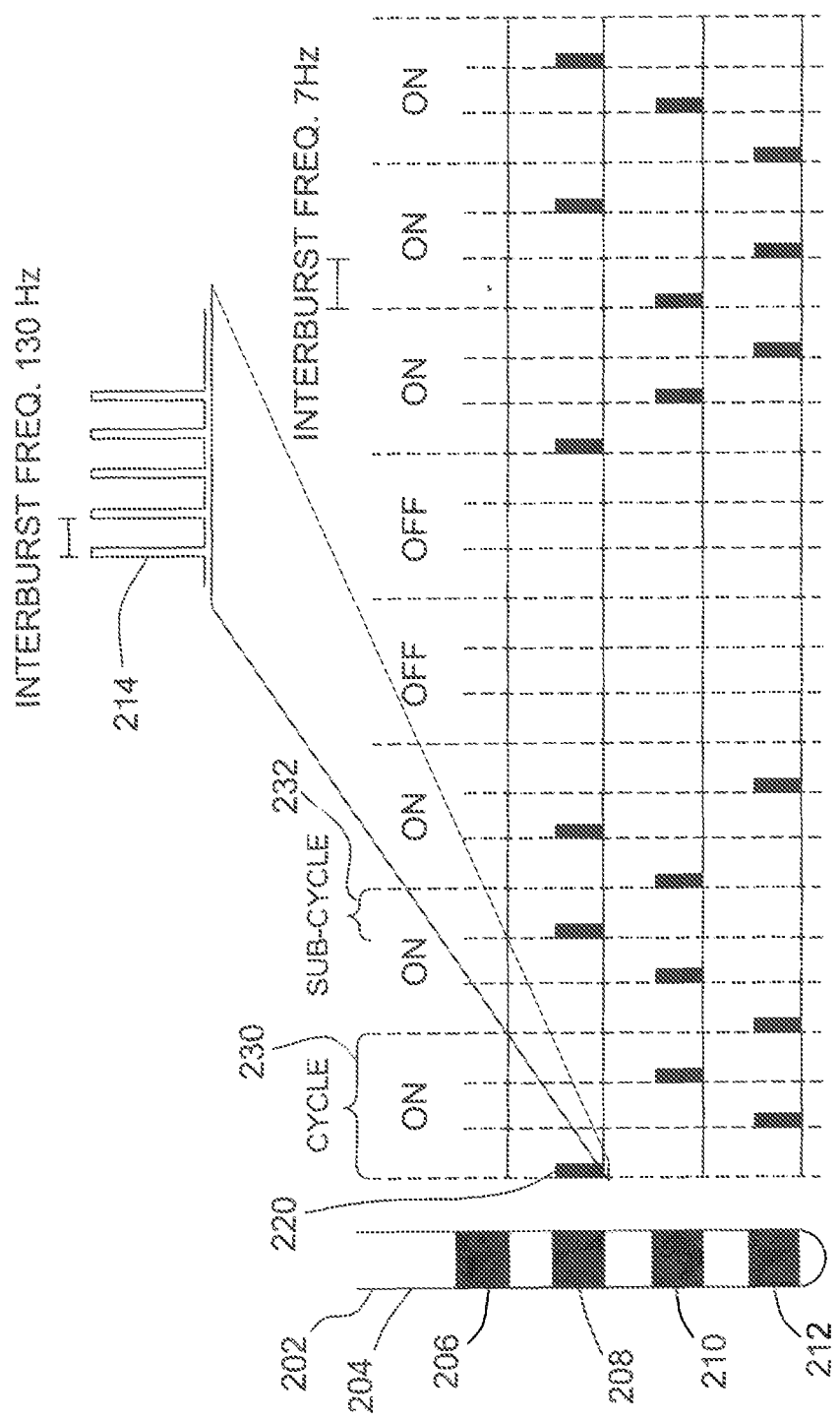
FIG. 3 is a schematic diagram illustrating one embodiment of application of random DBS using a stimulation lead.

FIG. 3 is a schematic diagram illustrating application of random DBS using stimulation lead 202. Stimulation lead 202 may be used, for example, with neurostimulation system 100 (shown in FIG. 1) to apply the random DBS.

As shown in FIG. 3, to apply random DBS, first contact 206 functions as an anode, and second, third and fourth contacts 208, 210, and 212 deliver bursts 220 of stimulation in a random or pseudorandom pattern. Alternatively, another of contacts 206, 208, 210, and 212 may function as the anode. In this embodiment, each burst 220 of stimulation includes multiple pulses 214 (e.g., five pulses 214) delivered at a constant intraburst frequency (e.g., 130 Hz). Alternatively, each burst 220 may include any number and arrangement of pulses 214 that enables stimulation lead 202 to function as described herein. That is, any suitable temporal arrangement of pulses within one burst 220 and/or any suitable spatial location of bursts 220 (i.e., the order in which contacts deliver subsequent bursts 220) may be utilized.

In this embodiment, random stimulation is delivered in cycles 230. A cycle 230 is the time duration during which a burst 220 is delivered from each of the available contacts 208, 210, and 212. A sub-cycle 232 is the time duration during which one of available contacts 208, 210, and 212 delivers a burst 220. In this embodiment, the random DBS includes a sequence of three ON cycles 230 followed by two OFF cycles 230 (i.e., cycles where no stimulation is delivered). Alternatively, the random DBS may include any suitable arrangement of ON and OFF cycles 230.

FIG. 4 is a schematic diagram illustrating application of a combination of tonic DBS and random DBS using stimulation lead 202. Stimulation lead 202 may be used, for example, with neurostimulation system 100 (shown in FIG. 1) to apply the combination of tonic and random DBS.

In the embodiment shown in FIG. 4, delay periods between subsequent bursts 220 of random stimulation are used to deliver tonic stimulation. Combining random stimulation and tonic simulation facilitates controlling symptoms and achieving sustained desynchronization of abnormal oscillations simultaneously. In this embodiment, first, second, and fourth contacts 206, 208, and 212 deliver random stimulation, and third contact 210 delivers tonic stimulation. Alternatively, any configuration of contacts 206, 208, 210, and 212 may be used to deliver the combination of random and tonic stimulation.

In one embodiment, to implement the combination of tonic DBS and random DBS shown in FIG. 4, IPG 150 generates, for each ON cycle 230, a random permutation of first, second, and fourth contacts 206, 208, and 212 (i.e., the contacts not selected for tonic stimulation). IPG 150 may use an internal timer to measure the time passed with each sub-cycle 232. Alternatively, IPG 150 may use the internal timer to measure a number of pulses 214 delivered as calculated from the intra-burst frequency, number of pulses 214 in a burst, and tonic DBS frequency. IPG 150 also uses a counter to keep track of the number of cycles 230 delivered.

At the beginning of an ON cycle 230, the internal timer is started and IPG 150 causes a burst 220 of stimulation including a predetermined number of pulses 214 (e.g., five pulses) to be delivered at the same frequency and pulse width identified for tonic DBS, but using the first contact in the random permutation of first, second, and fourth contacts 206, 208, and 212. For example, as shown in FIG. 4, IPG 150 causes second contact 208 to deliver a five-pulse burst 220 of stimulation.

After second contact 208 delivers burst 220, IPG 150 causes the contact selected for tonic DBS (i.e., third contact 210) to deliver tonic simulation until the internal timer determines the first sub-cycle 232 is complete. At that point, the internal timer is reset, and IPG 150 causes a burst 220 of stimulation to be delivered using the second contact in the random permutation of first, second, and fourth contacts 206, 208, and 212. For example, as shown in FIG. 4, IPG 150 causes fourth contact 212 to deliver a five-pulse burst 220 of stimulation.

After fourth contact 212 delivers burst 220, IPG 150 causes third contact 210 to deliver tonic simulation until the internal timer determines the second sub-cycle 232 is complete. At that point, the internal timer is reset, and IPG 150 causes a burst 220 of stimulation to be delivered using the third contact in the random permutation of first, second, and fourth contacts 206, 208, and 212. For example, as shown in FIG. 4, IPG 150 causes first contact 206 to deliver a five-pulse burst 220 of stimulation. After first contact 208 delivers burst 220, IPG 150 causes the contact selected for tonic DBS (i.e., third contact 210) to deliver tonic simulation until the internal timer determines the third sub-cycle 232 is complete, representing the end of the ON cycle 230.

At this point, the counter of IPG 150 is updated to reflect that one cycle 230 is complete, the internal timer is reset, and the next ON cycle 230 begins with a new permutation of first, second, and fourth contacts 206, 208, and 212 (i.e., the contacts not selected for tonic stimulation). This process repeats until a predetermined number of ON cycles 230 have been performed. Subsequently, IPG 150 causes the contact selected for tonic DBS (i.e., third contact 210) to deliver tonic simulation for a predetermined number of OFF cycles 230. Once the predetermined number of OFF cycles 230 are performed, the counter is reset, and the process repeats from the beginning (i.e., by starting an ON cycle 230).

In another embodiment, to implement a combination of tonic DBS and random DBS, IPG 150 includes an internal memory storing a script. The script may be, for example, computer-readable instructions. The script includes timing of each burst 220 of random stimulation and the corresponding channel (e.g., selected from channels for first, second, and fourth contacts 206, 208, and 212) used to deliver burst 220. When stimulation is initiated, an internal timer in IPG 150 is started, and the contact selected for delivering tonic stimulation (e.g., third contact 210) begins delivering tonic stimulation.

Tonic stimulation is delivered until the timing of a burst 220 specified in the script is reached, at which point the tonic DBS is temporarily stopped, and IPG 150 causes the burst 220 to be delivered using the channel indicated in the script (e.g., corresponding to one of first, second, and fourth contacts 206, 208, and 212).

As soon as the burst 220 is delivered, tonic stimulation resumes until the internal timer reaches the next timing specified in the script. Once the last timing in the script is reached, the internal timer is reset and the sequence repeats.

FIG. 5 is a schematic diagram illustrating application of a combination of tonic DBS and random DBS using stimulation lead 202 in accordance with an alternative embodiment. In the embodiment shown in FIG. 5, IPG 150 is capable of using multiple current sources. Accordingly, pulses 214 may be delivered simultaneously using multiple contacts.

In this embodiment, tonic stimulation is delivered continuously using the contact selected for tonic stimulation (e.g., third contract 210), and bursts 220 of random stimulation are delivered using the remaining contacts (e.g., first, second, and fourth contacts 206, 208, and 212) without interrupting the tonic stimulation. IPG 150 is programmed such that the contact selected for tonic stimulation delivers continuous tonic stimulation in accordance with predefined tonic DBS parameters (e.g., pulse width, amplitude, etc.). Further, IPG 150 is programmed such that the remaining contacts deliver random stimulation. In some embodiments, bursts 220 of random stimulation have different intensities, inter-burst frequencies, pulse widths, and/or number of pulses in a burst, depending on which contact is used to deliver the stimulation.

At the beginning of each ON cycle 230, the contact selected for tonic stimulation begins delivering continuous tonic stimulation. Further, at the beginning of each ON cycle 230, the order in which the remaining contacts apply bursts 220 of random stimulation is randomized, and the random DBS is delivered accordingly.

The embodiments described herein provide systems and methods for combining tonic and random stimulation in a deep brain stimulation (DBS) system. A stimulation lead includes a plurality of contacts. An implantable pulse generator (IPG) communicatively coupled to the stimulation lead causes tonic stimulation to be delivered using one contact of the plurality of contacts, and cause random stimulation to be delivered using a subset of the remaining contacts of the plurality of contacts. A subset may include all of the remaining contacts or less than all of the remaining contacts.

The systems and methods described herein facilitate improved symptom control while delivering random DBS. Further, benefits of tonic and random stimulation patterns are both achieved, facilitating sustained improvement in symptoms during periods where no stimulation is applied. The systems and methods described herein also facilitate saving battery power and increasing a therapeutic window, as low intensity stimulation is used. Using random stimulation also facilitates preventing patient adaptation to stimulation.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method of applying a combination of tonic stimulation and random stimulation using a deep brain stimulation (DBS) lead including a plurality of contacts to treat Parkinson's Disease (PD) in a patient, the method comprising:
   reducing PD-related tremor in the patient by delivering tonic stimulation using one contact of the plurality of contacts, wherein the tonic stimulation comprises a plurality of pulses with pulse parameters selected to reduce PD-related tremor in the patient; and
   reducing PD-related rigidity and bradykinesia in the patient by delivering random stimulation using a subset of the remaining contacts of the plurality of contacts, wherein the random stimulation is delivered using respective bursts of multiple pulses applied to randomly or pseudo-randomly selected contacts of the subset and wherein the random stimulation comprises pulses with pulse parameters selected to reduce PD-related rigidity and bradykinesia.

2. The method of claim 1, wherein delivering tonic and delivering random stimulation comprises delivering random stimulation in gaps between periods of tonic stimulation.

3. The method of claim 1, wherein delivering tonic and delivering random stimulation comprises delivering random stimulation without interrupting continuous tonic stimulation.

4. The method of claim 1, wherein delivering tonic and random stimulation comprises:
   delivering both random and tonic stimulation for a predetermined number of ON cycles; and delivering only tonic stimulation for a predetermined number of OFF cycles.

5. The method of claim 1 further comprising:
   operating an implantable pulse generator (IPG) with an internal timer to generate the tonic stimulation and the random stimulation, wherein the delivering tonic random stimulation comprises delivering random stimulation based on the internal timer of the IPG that measures the passing of sub-cycles.

6. The method of claim 1 further comprising:
   operating an implantable pulse generator (IPG) with a script stored in internal memory of the IPG, wherein the delivering tonic random stimulation comprises delivering random stimulation based on the script stored in the internal memory of the IPG, the script including timing of a plurality of bursts of random stimulation and an associated contact for each burst.

7. The method of claim 1 wherein the tonic stimulation comprises a continuous train of stimulation pulses with a stimulation frequency between 130 Hz and 180 Hz that is sufficiently long to suppress PD-related tremor in the patient.

* * * * *